United States Patent
Leneau

(10) Patent No.: US 6,607,745 B2
(45) Date of Patent: Aug. 19, 2003

(54) INGESTION OF HYALURONIC ACID FOR IMPROVED JOINT FUNCTION AND HEALTH

(76) Inventor: Harry Leneau, 18753 County La. 170, Jasper, MO (US) 64755-9802

(*) Notice: Subject to any disclaimer, the term of this patent is extended or adjusted under 35 U.S.C. 154(b) by 0 days.

(21) Appl. No.: 09/860,425

(22) Filed: May 18, 2001

(65) Prior Publication Data

US 2002/0173484 A1 Nov. 21, 2002

(51) Int. Cl.$^7$ ............................................... A61K 47/00
(52) U.S. Cl. ........................ 424/439; 424/400; 424/442; 424/451; 424/452; 514/825
(58) Field of Search ................... 424/400, 439, 424/442, 451, 452; 514/825

(56) References Cited

U.S. PATENT DOCUMENTS

| | | |
|---|---|---|
| 4,808,576 A | 2/1989 | Schultz et al. |
| 5,470,578 A | 11/1995 | Aoki et al. |
| 5,633,003 A | 5/1997 | Cantor |
| 6,037,331 A * | 3/2000 | Shalaby et al. ............... 514/54 |
| 6,159,955 A | 12/2000 | Asculai et al. |
| 2002/0012690 A1 * | 1/2002 | Yoshimura et al. ......... 424/442 |

FOREIGN PATENT DOCUMENTS

JP 06107550 A * 4/1994 ......... A61K/31/725

OTHER PUBLICATIONS

"Hyaluronan (Hyaluronic acid, Synvise, Hyalgan)" from website www.midwestarthritis.com/html/hyaluronic$_{13}$acid.htm.

Wen, Dennis Y., "Intra-articular Hyaluronic Acid Injections for Knee Osteoarthritis", *American Family Physician*, 60, 565–70,572, (2000).

Marte, Jim, "Green Plaster, A Webpage Resource For Orthopaedic Technolgists. Intra–Articular Hyaluronic Acid Injections for Knee Osteoarthritis", from website home.earthlink.net/~jim56/otchyal.html.

"Arthritic Disorders", www.advanhealth.com/arthritis.htm.

"Arthritic Disorders and Treatments", from website www-.s.org/brarthdis.html.

"Hillbrook Wellness Institute", from website www.hillbrook.com.

"Glucosamine and Chondroitin", from website chemistry-.about.com/science/chemistry/library/weekly/aa120400a.htmi, (12/00).

"Fibromyalgia Basics—Symptoms, Treatments and Research", from website www.fmnetnews.com/pages/basics.html.

"Hyaluronic Acid (Hyaluronan)", from website www.apharma.it/site/html/hyaluronic.htm.

"Hyaluronic Acid", from website www.bioiberica.com/eng/mp/hyaluronic.htm.

"Hyaluronic acid", from website www.medmedia.com/02/68.htm.

"Hyaluronic Acid" from website uconnsportsmed.uchc.edu/hyaluronic$_{13}$ acid.htm.

* cited by examiner

*Primary Examiner*—Thurman K. Page
*Assistant Examiner*—Charesse L. Evans
(74) *Attorney, Agent, or Firm*—Barnes & Thornburg

(57) ABSTRACT

Methods are described for relieving discomforts associated with osteoarthritis or fibromyalgia. The methods comprise the step of delivering by oral ingestion a nutritional supplement consisting essentially of an effective amount of hyaluronic acid, or a salt or digest thereof, and a food acceptable carrier, wherein the effective amount of hyaluronic acid, or a salt or digest thereof, is from about 0.1 μg to about 400 μg/kg of body weight.

7 Claims, No Drawings

INGESTION OF HYALURONIC ACID FOR IMPROVED JOINT FUNCTION AND HEALTH

FIELD OF THE INVENTION

The present invention relates to a method for relieving joint pain or other discomfort in a warm-blooded vertebrate. More particularly, this invention provides relief of symptoms of arthritic disorders or fibromyalgia by oral ingestion of a composition comprising an effective amount of hyaluronic acid, or a salt or digest thereof.

BACKGROUND AND SUMMARY OF THE INVENTION

Arthritic disorders, including acute and chronic rheumatoid arthritis and osteoarthritis as well as inflammatory skeletal and musculoskeletal conditions, affect millions of people. It has been estimated that 80% of all individuals over the age of 55 suffer from some form of arthritic disorder. The most common arthritic disorder is osteoarthritis. Osteoarthritis develops gradually over time in many cases. Patients experience alternating periods of mild to moderate pain, stiffness, and swelling of the joint and periods of relatively symptom-free joint activity. Osteoarthritis is characterized by the deterioration of cartilage that covers the ends of bones at a joint, such as the knee or hip. In the healthy joint, cartilage acts as a shock absorber and aids the joint in bearing the stress of physical movement. In addition, synovial joint fluid produced by the synovial membrane lubricates the joint providing a slippery surface over which the bones may move. But as cartilage deteriorates, the bones begin to rub against each other causing joint pain.

At the same time, the concentration of hyaluronic acid in the synovial joint decreases, reducing the lubrication ability of the synovial joint fluid. Also, joint movement may be restricted as bone ends erode or thicken, and the bones may develop painful outgrowths, or bone spurs, as a result of this erosion or thickening. If left untreated, cartilage deterioration can seriously weaken the joint, possibly to the point of deformity.

Current methods of reducing pain in osteoarthritic joints include treatment with analgesics or anti-inflammatory medications, physical therapy, topical application of hyaluronic acid to the joint, and intra-articular injection of hyaluronic acid directly into the joint. The primary goal of treatment is reduction of pain and maintenance of joint function and strength. Intra-articular injections of hyaluronic acid, known as viscosupplementation, have seen wide use for patients who have not responded well to other therapies.

Fibromyalgia is a common disabling disorder characterized by chronic musculoskeletal aches and pain, stiffness, general fatigue, and sleep abnormalities. The disorder affects 2–4% of the population and is most frequently found in women between 20 and 50 years old. The exact cause of fibromyalgia remains uncertain, and diagnosis is difficult due to the general nature of the symptoms. Currently, the most effective treatment for fibromyalgia includes a combination of analgesics, sleep aids, exercise programs, relaxation techniques and other measures to reduce muscle tension. These treatments are geared toward improving sleep quality and reducing pain.

The present invention is directed to a method for relieving joint and musculoskeletal discomfort in warm-blooded vertebrates comprising the step of delivering to the vertebrate by oral ingestion a composition comprising an effective amount of hyaluronic acid, or a salt or digest thereof, and an acceptable ingestible carrier. The method is used with advantage in treating conditions associated with osteoarthritis and for reducing the discomfort of fibromyalgia in a person afflicted with fibromyalgia.

DETAILED DESCRIPTION OF THE INVENTION

Hyaluronic acid is a mucopolysaccharide that is found in joint tissue and in the vitreous humor of the eye. Hyaluronic acid functions as a protective coating and a lubricant for soft tissue and joints, and additionally, helps maintain the structural integrity of soft tissue. In association with protein, hyaluronic acid binds water in the intercellular spaces and holds cells together in a jellylike matrix. This jellylike matrix provides lubrication and shock absorption throughout the body.

In the healthy knee joint, hyaluronic acid is present both in the cartilage covering the ends of bone and in the synovial joint fluid. Hyaluronic acid is usually found as part of proteoglycan aggregates in cartilage, where it helps cartilage withstand forces of weight bearing and joint movement. Hyaluronic acid is also a major component of synovial joint fluid. The synovial joint fluid provides lubrication for the cartilage against the lining of the joint and may provide some additional shock-absorption value.

Hyaluronic acid is commercially available and is prepared from the intracellular matrices of animal connective tissue, such as rooster combs and bovine tissue sources, mammalian umbilical cords, and bacterial organisms such as streptococcus zoepidicus. Its molecular weight ranges from about 50000 to about $8 \times 10^6$ Daltons depending on source and method of isolation. Treatment with hyaluronidases can be used to provide hydrolysates of reduced molecular weight range.

The present method provides relief from joint pain and musculoskeletal discomfort in a warm-blooded vertebrate suffering from an arthritic condition or fibromyalgia. An arthritic condition includes acute and chronic rheumatoid arthritis and osteoarthritis, as well as inflammatory conditions involving skeletal conditions and musculoskeletal conditions.

In accordance with the present invention, a method is provided for relieving joint or musculoskeletal pain or discomfort in a warm-blooded vertebrate comprising delivering to the vertebrate by oral ingestion a composition comprising an effective amount of hyaluronic acid, or a salt or digest thereof, and a nutritionally acceptable carrier. An "effective amount" as used herein refers to the amount of hyaluronic acid which, upon oral administration, provides relief of joint pain or discomfort. The effective amount of hyaluronic acid, or a salt or digest thereof, is from about 0.1 µg/kg to about 400 µg/kg of body weight per dose. The warm-blooded vertebrate may be a human, or an equine, canine, or feline species. In one embodiment the method is used to reduce joint pain n a person afflicted with osteoarthritis.

In another embodiment the method is used for reducing the discomfort of fibromyalgia. The hyaluronic acid, salt or digest is orally ingested with a acceptable carrier, typically an aqueous beverage or food product. Preferably, the hyaluronic acid, salts or hydrolysates for use in the present invention is formulated into a liquid aqueous concentration, for example, a dietary supplement formulation, which is diluted in portions and mixed with food, water, or other beverages for oral ingestion. Alternatively the hyaluronic acid, salt, or hydrolysate can be packaged in individual solid or liquid doses, for instance in capsules or gel seals. The concentrate can contain about 1 to about 10 mg of hyaluronic acid, its salt or hydrolysate per milliliter of concentrate. In one embodiment a dose is administered by combining 7 to 10 drops of the concentrate in a cold beverage which is consumed on conjunction with a meal, for example.

EXAMPLES

Example 1

Oral Ingestion of Hyaluronic Acid By Patients Suffering From Osteoarthritis

A study involving sixty-seven patients suffering from osteoarthritis was undertaken to determine the effectiveness of oral ingestion of hyaluronic acid. Each patient received 1–4 mg of hyaluronic acid by oral ingestion administration 1 to 4 times a day over periods ranging from about 4 to about 2 weeks, during which period the patients' subjective pain feeling was reported. Twenty-nine patients (43.3%) reported no pain after oral ingestion of hyaluronic acid, and additionally reported increased range of motion. Twenty-four patients reported (35.8%) some degree of pain relief and some increased range of motion. Fourteen patients reported no change in the amount of pain they felt.

Example 2

Oral Ingestion of Hyaluronic Acid by Patients Afflicted With Fibromyalgia

Another study involving thirty-five human patients suffering pain and discomfort associated with fibromyalgia was undertaken to evaluate the effectiveness of oral ingestion of hyaluronic acid. Each patient received about 1 to about 6 mg of hyaluronic acid by oral ingestion administration of concentrate diluted into beverages or food. Over a treatment period of about 1 to about 14 months, the patients' subjective pain feeling was reported. Twenty-one patients reported no pain after hyaluronic acid therapy. Six patients (17.1%) reported some (60%) degree of pain relief. Eight patients reported no change in the amount of pain they felt.

What is claimed is:

1. A method for relieving joint pain or other discomforts associated with osteoarthritis in a warm-blooded vertebrate comprising the step of delivering to said vertebrate by oral ingestion a nutritional supplement consisting essentially of an effective amount of hyaluronic acid, or a salt or digest thereof, and a food acceptable carrier, wherein the effective amount of hyaluronic acid, or a salt or digest thereof, is from about 0.1 $\mu$g to about 400 $\mu$g/kg of body weight.

2. The method of claim 1 further comprising the step of adding the hyaluronic acid, or a salt or digest thereof, to the carrier, and wherein the carrier comprises food or water.

3. The method of claim 1 wherein the nutritional supplement is provided in capsule form.

4. The method of claim 1 wherein the warm-blooded vertebrate is a human, or an equine, canine, or feline species.

5. A method for reducing discomfort of fibromyalgia in a person afflicted with fibromyalgia comprising the step of delivering to said person by oral ingestion a nutritional supplement consisting essentially of an effective amount of hyaluronic acid, or a salt or digest thereof, and a nutritionally acceptable carrier, wherein the effective amount of hyaluronic acid, or a salt or digest thereof, is from about 0.1 $\mu$g to about 400 $\mu$g/kg of body weight.

6. The method of claim 5 further comprising the step of adding the hyaluronic acid, or a salt or digest thereof, to the carrier, and wherein the carrier comprises food or water.

7. The method of claim 5 wherein the nutritional supplement is provided in capsule form.

* * * * *